United States Patent [19]

Zondler

[11] Patent Number: 5,120,741

[45] Date of Patent: Jun. 9, 1992

[54] MICROBICIDES

[75] Inventor: Helmut Zondler, Bottmingen, Switzerland

[73] Assignee: Ciba-Geigy Corporation, Ardsley, N.Y.

[21] Appl. No.: 648,952

[22] Filed: Feb. 1, 1991

[30] Foreign Application Priority Data

Feb. 7, 1990 [CH] Switzerland ............................. 388/90

[51] Int. Cl.$^5$ ................... C07D 239/42; A01N 43/54; C07F 7/10; C07F 9/09
[52] U.S. Cl. ...................... 514/275; 514/63; 514/85; 544/332; 544/229; 544/243
[58] Field of Search ............... 514/275, 63, 85; 544/332, 229, 243

[56] References Cited

U.S. PATENT DOCUMENTS 4,966,622 10/1990 Rempfler et al. .................... 71/92

FOREIGN PATENT DOCUMENTS 0243136 10/1981 European Pat. Off. .
0270111 6/1988 European Pat. Off. .
0337943 10/1989 European Pat. Off. .

Primary Examiner—John M. Ford
Attorney, Agent, or Firm—Marla J. Mathias; Edward McC. Roberts

[57] ABSTRACT

Compounds of the formula

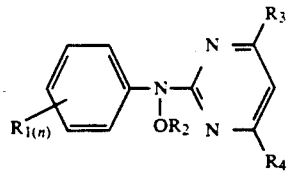

in which $R_1$ is hydrogen, halogen, methyl, methoxy or trifluoromethyl; n is 1 or 2; $R_2$ is hydrogen, $C_1$-$C_6$alkyl, $C_1$-$C_3$alkyl which is substituted by halogen, cyano or methoxy, or is $C_2$-$C_5$alkenyl, $C_2$-$C_5$alkynyl, benzyl, $COR_5$, $CON(R_5)R_6$, $CSN(R_5)R_6$, $CO(OR_6)$, $CO(SR_6)$, $CS(SR_5)$, $SO_2R_7$, $PO(OR_6)_2$ or $Si(R_6)_3$; $R_3$ and $R_4$ independently of one another are hydrogen, $C_1$-$C_5$alkyl, $CH_2OR_6$, cyclopropyl, methylcyclopropyl, $C_2$-$C_5$alkenyl, $C_2$-$C_5$alkynyl or $C_1$-$C_2$haloalkyl; $R_5$ is hydrogen, $C_1$-$C_6$alkyl, $C_1$-$C_3$alkyl which is substituted by 1 to 3 halogens, $C_1$-$C_3$alkyl which is substituted or $OR_6$ or $SR_6$, or is $C_2$-$C_5$alkenyl, $C_2$-$C_5$alkenyl which is substituted by 1 to 3 halogens, $C_2$-$C_5$alkynyl, $C_3$-$C_6$cycloalkyl, phenyl or phenyl which is monosubstituted to trisubstituted by halogen, $C_1$-$C_3$alkyl, $C_1$-$C_3$haloalkyl, $C_1$-$C_3$alkoxy, nitro or cyano; $R_6$ is $C_1$-$C_6$alkyl; $R_7$ is $C_1$-$C_3$alkyl, phenyl, phenyl which is monosubstituted or disubstituted by halogen, $C_1$-$C_2$alkyl, $C_1$-$C_2$haloalkyl, methoxy or nitro; including the acid addition salts, have valuable microbicidal properties. The novel active substances can be employed in crop protection for preventing crop plants being attacked by phytopathogenic microorganisms, and for controlling these pests.

14 Claims, No Drawings

MICROBICIDES

The present invention relates to novel pyrimidinyl-phenylhydroxylamine derivatives of the formula I below. It furthermore relates to the preparation of these substances and to agrochemical compositions which comprise at least one of these compounds as active substance. The invention likewise relates to the preparation of the compositions mentioned, and to the use of the active substances or of the compositions for controlling or preventing an attack on plants by phytopathogenic microorganisms, notably fungi.

The compounds according to the invention are those of the general formula I

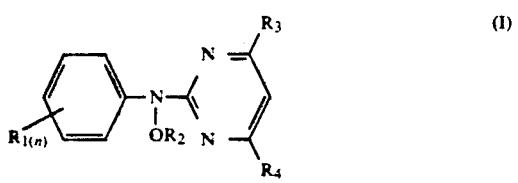

in which $R_1$ is hydrogen, halogen, methyl, methoxy or trifluoromethyl; n is 1 or 2; $R_2$ is hydrogen, $C_1$-$C_6$alkyl, $C_1$-$C_3$alkyl which is substituted by halogen, cyano or methoxy, or is $C_2$-$C_5$alkenyl, $C_2$-$C_5$alkynyl, benzyl, $COR_5$, $CON(R_5)R_6$, $CSN(R_5)R_6$, $CO(OR_6)$, $CO(SR_6)$, $CS(SR_5)$, $SO_2R_7$, $PO(OR_6)_2$ or $Si(R_6)_3$; $R_3$ and $R_4$ independently of one another are hydrogen, $C_1$-$C_5$alkyl, $CH_2OR_6$, cyclopropyl, methylcyclopropyl, $C_2$-$C_5$alkenyl, $C_2$-$C_5$alkynyl or $C_1$-$C_2$haloalkyl; $R_5$ is hydrogen, $C_1$-$C_6$alkyl, $C_1$-$C_3$alkyl which is substituted by 1 to 3 halogens, $C_1$-$C_3$alkyl which is substituted by $OR_6$ or $SR_6$, or is $C_2$-$C_5$alkenyl, $C_2$-$C_5$alkenyl which is substituted by 1 to 3 halogens, $C_2$-$C_5$alkynyl, $C_3$-$C_6$cycloalkyl, phenyl or phenyl which is monosubstituted to trisubstituted by halogen, $C_1$-$C_3$alkyl, $C_1$-$C_3$haloalkyl, $C_1$-$C_3$alkoxy, nitro or cyano; $R_6$ is $C_1$-$C_6$alkyl; $R_7$ is $C_1$-$C_3$alkyl, phenyl, phenyl which is monosubstituted or disubstituted by halogen, $C_1$-$C_2$alkyl, $C_1$-$C_2$haloalkyl, methoxy or nitro; including the acid addition salts of the compounds of the formula I.

The term alkyl itself or as a component of another substituent is to be understood as meaning, depending on the number of carbon atoms indicated, for example the following groups: methyl, ethyl, propyl, butyl, pentyl or hexyl, and, for example, their isomers isopropyl, isobutyl, tert-butyl, sec-butyl, isopentyl etc. Alkenyl is, for example, propen-1-yl, allyl, buten-1-yl, buten-2-yl or buten-3-yl. Halogen here and in what follows is taken to mean fluorine, chlorine, bromine or iodine, preferably fluorine, chlorine or bromine.

At room temperature, the compounds of the formula I are stable oils, resins or solid substances which are distinguished by very valuable physiological, such as microbicidal, for example phytofungicidal, properties. They can therefore be employed on the one hand in the agricultural sector or in related fields for controlling phytopathogenic microorganisms, in particular fungi.

The invention relates to the free compounds of the formula I and to their acid addition salts with organic and inorganic acids.

Salts according to the invention are, in particular, addition salts with inorganic or organic acids which are biocompatible, depending on the intended use, for example hydrohalic acids, for example hydrochloric acid, hydrobromic acid or hydriodic acid, and also sulfuric acid, phosphoric acid, phosphorous acid, nitirc acid, halogenated or unhalogenated fatty acids such as acetic acid, trichloroacetic acid and oxalic acid, or sulfonic acids such as benzenesulfonic acid and methanesulfonic acid, and also addition salts with suitable salts, for example magnesium chloride or calcium chloride.

The following groups of active substances are preferred because of their pronounced plant-protecting properties:

a) compounds of the formula I in which $R_1$ is hydrogen, fluorine, chlorine or bromine; n is 1; $R_2$ is hydrogen, $C_1$-$C_4$alkyl, $C_1$-$C_3$alkenyl, $C_1$-$C_3$alkynyl, $COR_5$, $CON(R_5)R_6$, $CSNR_5(R_6)$ or $COOR_6$; $R_3$ and $R_4$ independently of one another are hydrogen, $C_1$-$C_5$alkyl, methoxymethyl, cyclopropyl or methylcyclopropyl; $R_5$ is hydrogen, $C_1$-$C_6$alkyl, $C_3$-$C_6$cycloalkyl, $C_2$-$C_5$alkenyl, $C_2$-$C_5$alkynyl, phenyl, or phenyl which is monosubstituted by fluorine, chlorine, bromine, methyl, trifluoromethyl, trichloromethyl, tribromomethyl, methoxy, nitro or cyano; and $R_6$ is $C_1$-$C_3$alkyl.

b) Compounds of the formula I in which $R_1$ is hydrogen, fluorine or chlorine; n is 1; $R_2$ is hydrogen, $C_1$-$C_3$alkyl, $COR_5$, $CON(R_5)R_6$, $CSNR_5(R_6)$ or $COOR_6$; $R_3$ and $R_4$ independently of one another are $C_1$-$C_3$alkyl, methoxymethyl, cyclopropyl or methylcyclopropyl; $R_5$ is hydrogen or $C_1$-$C_4$alkyl; and $R_6$ is $C_1$-$C_3$alkyl.

The following compounds are distinguished by particularly advantageous plant-protecting properties:

N-(4,6-dimethylpyrimidin-2-yl)-phenylhydroxylamine (comp. No. 1.1);

N-(4,6-dimethylpyrimidin-2-yl)-3-fluorophenylhydroxylamine (comp. No. 1.6);

N-(4-methyl-6-cyclopropylpyrimidin-2-yl)-phenylhydroxylamine (comp. No. 1.13);

N-(4-methyl-6-cyclopropylpyrimidin-2-yl)-3-fluorophenylhydroxylamine (comp. No. 1.16);

N-(4-methyl-6-methoxymethylpyrimidin-2-yl)-phenylhydroxylamine (comp. No. 1.61);

N-(4-methyl-6-methoxymethylpyrimidin-2-yl)-3-fluorophenylhydroxylamine (comp. No. 1.27);

O-acetyl-N-(4-methyl-6-cyclopropylpyrimidin-2-yl)-phenylhydroxylamine (comp. No. 1.26);

O-pivaloyl-N-(4-methyl-6-cyclopropylpyrimidin-2-yl)-phenylhydroxylamine (comp. No. 1.36).

The compounds of the formula I are prepared by reacting:

A) a pyrimidinyl halide of the formula II

with a phenylhydroxylamine of the formula III

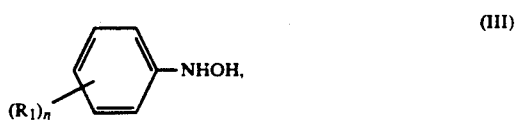

in which $R_1$, $R_3$ and $R_4$ and n are as defined under formula I and Hal is a halogen, preferably chlorine or bromine, in the presence of an acid in inert organic solvents, at temperatures from −30° to 100° C., preferably 0° to 50° C.; and B) the resulting compound Ia

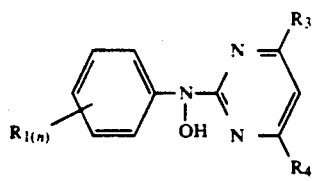

(Ia)

C) with a compound of the formula IV

R$_2$—X       (IV), in which R$_1$, R$_2$, R$_3$, R$_4$ and n are as defined under formula I and X is halogen, preferably chlorine or bromine, or the imidazolyl radical; or D) with an anhydride of the formula V (R$_5$CO)O       (V);

or

E) with an isocyanate of the formula VI

R$_5$—N=C=Y       (VI), in which Y is oxygen or sulfur, in inert organic solvents, at temperatures from −20° to 150° C., preferably 0° to 100° C., and, as regards reactions (C) and (D), in the presence of an acid-binding agent.

Examples of suitable reaction media which can be used depending on the particular reaction conditions are the following solvents and diluents: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ether-like compounds such as dialkyl ethers (diethyl ether, diisopropyl ether, tert-butyl methyl ether etc.), anisole, dioxane, tetrahydrofuran; nitriles such as acetonitrile, propionitrile; N,N-dialkylated amides such as dimethylformamide; furthermore dimethyl sulfoxide or N-methylpyrrolidone; and mixtures of such solvents with one another.

Acids which are used are inorganic and also organic acids, for example hydrohalic acids, for example hydrofluoric acid, hydrochloric acid or hydrobromic acid, and sulfuric acid, phosphoric acid or nitric acid, and, for example, acetic acid, formic acid, oxalic acid, citric acid, trifluoroacetic acid, methanesulfonic acid or toluenesulfonic acid.

Substances which act as acid-binding agents are proton acceptors, mainly organic bases, for example tertiary amines, for example triethylamine, dimethylaminobenzene, diethylaminobenzene or pyridine, and organic bases, for example alkali metal compounds or alkaline earth metal compounds, for example the hydroxides, oxides or carbonates of lithium, sodium, potassium, magnesium, calcium, strontium and barium, and also hydrides, for example sodium hydride.

The 2-halopyrimidines of the formula II are known or can be prepared by methods known to those skilled in the art (for reference, cf. D. J. Brown, The Pyrimidines in Heterocyclic Compounds, 1962, Interscience Publishers, New York). In particular 2-chloropyrimidines are used in the process according to variant (A) described above.

The phenylhydroxylamines of the formula III are prepared by reducing nitrobenzene derivatives with hydrazine hydrate in the presence of rhodium catalysts (for reference, cf. Oxley, Organic Synthesis 67, 187).

4,6-Disubstituted-2-phenylamino pyrimidine derivatives are known from the literature. Such substances are described, for example, in European Patent Applications No. 243,136 and No. 270,111 as active ingredients against harmful microorganisms, which also include phytopathogenic fungi. However, these substances do not always meet the requirements which are demanded in practice.

Surprisingly, it has now been found that compounds of the formula I have a biocidal spectrum for controlling insects and phytopathogenic microorganisms, in particular fungi, which is very favourable for requirements in practice. They have very advantageous curative, preventive and, in particular, systemic properties, and are employed for protecting a large number of crop plants. Using the active substances of the formula I, the pests which occur can be restrained or destroyed on plants or parts of plants (fruits, flowers, foliage, stalks, tubers, roots) of various crops, parts of plants which grow later also remaining free from, for example, phytopathogenic microorganisms.

Compounds of the formula I are effective for example against the phytopathogenic fungi which belong to the following classes: *Fungi imperfecti* (in particular Botrytis, furthermore Pyricularia, Helminthosporium, Fusarium, Septoria, Cercospora and Alternaria); Basidiomycetes (for example Rhizoctonia, Hemileia, Puccinia). Moreover, they are also active against the class of the Ascomycetes (for example Venturia and Erysiphe, Podosphaera, Monilinia, Uncinula) and of the Oomycetes (for example Phytophthora, Pythium, Plasmopara). Furthermore, the compounds of the formula I can be employed as seed-dressing agents for treating seed (fruits, tubers, grains) and cuttings of plants for protecting them from fungal infections and against phytopathogenic fungi which occur in the soil.

The invention also relates to those compositions which comprise compounds of the formula I as active substance component, in particular to plant-protecting compositions, and to their use in the agricultural sector or in related fields.

In addition, the present invention also embraces the preparation of these compositions, in which the active ingredient is mixed intimately with one or more substances or substance groups described in this publication. A method of treating plants, which is distinguished by applying the novel compounds of the formula I or the novel compositions, is also embraced.

Within the scope of this invention, target crops for the plant-protecting application disclosed in this publication are, for example, the following plant species: cereals (wheat, barley, rye, oats, rice, maize, sorghum and related species); beet (sugar beet and fodder beet); pomaceous fruit, stone fruit and soft fruit (apples, pears, plums, peaches, almonds, cherries, strawberries, raspberries and blackberries); pulses (beans, lentils, peas, soya); oil crops (oilseed rape, mustard, poppy, olives, sunflowers, coconut, castor, cocoa, peanuts); cucurbits (pumpkin, cucumber, melons); fibrous plants (cotton, flax, hemp, jute); citrus fruit, (oranges, lemons, grapefruit, tangerines); various vegetables (spinach, lettuce, asparagus, cabbage species, carrots, onions, tomatoes, potatoes, capsicums): Lauraceae (avocado, cinnamomum, camphor), or plants such as tobacco, nuts, coffee, sugar cane, tea, pepper, grapevines, hops, Musaceae and plants which produce natural latex, and also ornamentals.

Active substances of the formula I are customarily used in the form of combinations and can be applied to the area or plant to be treated simultaneously with other active substances, or in succession. These other active substances can be fertilisers, trace element sources or other preparations which influence plant growth. It is also possible to use in this context selective herbicides and insecticides, fungicides, bactericides, nematicides, molluscicides or mixtures of several of these preparations, if desired together with other carriers, surfactants or other application-enhancing additives which are conventionally used in the art of formulation.

Suitable carriers and additives can be solid or liquid and correspond to the substances which are expedient in the art of formulation, for example natural or regenerated mineral substances, solvents, dispersants, wetting agents, tackifiers, thickeners, binders or fertilisers.

A preferred method of applying an active substance of the formula I or an agrochemical composition which comprises at least one of these active substances, is application to the foliage (foliar application). The frequency of application and the amount applied depend on the risk of infestation by the particular pathogen. Alternatively, the active substances of the formula I can also reach the plant via the soil through the roots (systemic action) by drenching the site where the plant grows with a liquid preparation, or incorporating the substances into the soil in solid form, for example in the form of granules (soil application). In the case of paddy rice cultures such granules can be metered into the flooded rice field. Alternatively, the compounds of the formula I can also be applied to seed grains (coating), either by soaking the grains in a liquid preparation of the active substance or by coating them with a solid preparation.

The compounds of the formula I are employed as pure active substances or, preferably, together with the auxiliaries conventionally used in formulation technology. For this purpose, they are expediently processed in a known manner to give, for example, emulsion concentrates, spreadable pastes, directly sprayable or dilutable solutions, diluted emulsions, wettable powders, soluble powders, dusts, granules, for example by encapsulations in polymeric substances. The application methods such as spraying, atomising, dusting, scattering, brushing on or pouring, as well as the nature of the compositions, are selected to suit the intended aims and the prevailing circumstances.

Favourable application rates are generally 10 g to 5 kg of active ingredient (a.i.) per ha, preferably 20 g to 1 kg of a.i./ha.

The formulations, i.e. the compositions, preparations or combinations comprising the active substance of the formula I and, if desired, a solid or liquid additive, are prepared in a known manner, for example by intimately mixing and/or grinding the active substances with extenders, for example with solvents, solid carriers and, if desired, surface-active compounds (surfactants).

The following are possible as solvents: aromatic hydrocarbons, preferably the fractions $C_8$ to $C_{12}$, for example xylene mixtures or substituted naphthalenes, phthalic esters, such as dibutyl phthalate or dioctyl phthalate, aliphatic hydrocarbons, such as cyclohexane or paraffins, alcohols and glycols as well as their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, and also epoxidized or unepoxidized vegetable oils, such as epoxidized coconut oil or soya oil; or water.

Solid carriers which are used as a rule, for example for dusts and dispersible powders, are ground natural minerals, such as calcite, talc, kaolin, montmorillonite or attapulgite. To improve the physical properties, it is also possible to add highly-disperse silicas or highly-disperse absorptive polymers. Possible particulate, adsorptive carriers for granules are either porous types, for example pumice, brick grit, sepiolite or bentonite, or non-sorptive carrier materials, such as calcite or sand. Moreover, a large number of pregranulated materials of organic and inorganic nature can be used, such as, in particular, dolomite or comminuted plant residues.

Particularly advantageous application-enhancing adjuvants which can lead to a substantial reduction in the application rate are furthermore natural phospholipids (of animal or vegetable origin) or synthetic phospholipids.

Suitable surface-active compounds are non-ionic, cationic and/or anionic surfactants having good emulsifying, dispersing and wetting properties, depending on the nature of the active substance of the formula I to be formulated. Surfactants are also to be understood as meaning mixtures of surfactants.

Anionic surfactants which are suitable can be either so-called water-soluble soaps or water-soluble synthetic surface-active compounds.

Suitable soaps which may be mentioned are the alkali metal salts, alkaline earth metal salts or substituted or unsubstituted ammonium salts of higher fatty acids ($C_{10}$–$C_{22}$), such as the sodium salts or potassium salts of oleic or stearic acid, or of natural mixtures of fatty acids which can be obtained, for example, from coconut or tallow oil. Mention must also be made of the fatty acid methyltaurides.

However, so-called synthetic surfactants are used more frequently, in particular alkanesulfonates, fatty alcohol sulfates, sulfonated benzimidazole derivatives or alkylsulfonates.

The fatty alcohol sulfonates or fatty alcohol sulfates are, as a rule, in the form of alkali metal salts, alkaline earth metal salts or substituted or unsubstituted ammonium salts, and have an alkyl radical having 8 to 22 C atoms, alkyl also including the alkyl moiety of acyl radicals, for example the sodium or calcium salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2-sulfonyl groups and one fatty acid radical having 8 to 22 C atoms. Examples of alkylarylsulfonates are the sodium, calcium or triethanolamine salts of dodecylbenzenesulfonic acid, of dibutylnaphthalenesulfonic acid or of a naphthalenesulfonic acid/formaldehyde condensation product.

Other suitable compounds are the corresponding phosphates, such as the salts of the phosphoric ester of a p-nonylphenol/(4–14)-ethylene oxide adduct.

Suitable non-ionic surfactants are mainly polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other non-ionic surfactants which are suitable are the water-soluble polyethylene oxide adducts with polypropylene glycol, ethylenediaminopolypropylene glycol and alkylpolypropylene glycol which have 1 to 10 carbon atoms in the alkyl chain and which contain 20 to 250 ethylene glycol ether groups and 10 to 100 propylene glycol ether groups. The abovementioned compounds customarily contain 1 to 5 ethylene glycol units per propylene glycol unit.

Examples of non-ionic surfactants which may be mentioned are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Other suitable substances are fatty acid esters of polyoxyethylenesorbitan, such as polyoxyethylenesorbitan trioleate.

The cationic surfactants are mainly quaternary ammonium salts which contain at least one alkyl radical having 8 to 22 C atoms as N-substituents and which have lower halogenated or free alkyl, benzyl or lower hydroxyalkyl radicals as further substituents. The salts are preferably in the form of halides, methyl sulfates or ethyl sulfates, for example stearyltrimethylammonium chloride or benzyldi(2-chloroethyl)ammonium bromide.

Other surfactants customary in formulation technology are known to those skilled in the art or can be found in the relevant specialist literature.

As a rule, the agrochemical preparations contain 0.1 to 99%, in particular 0.1 to 95%, of the active substance of the formula I, 99.9 to 1%, in particular 99.9 to 5%, of a solid or liquid additive and 0 to 25%, in particular 0.1 to 25%, of a surfactant.

While concentrated compositions are preferred as commercial goods, the end user normally uses dilute compositions.

The compositions can also contain further additives, such as stabilizers, defoamers, viscosity regulators, binders, tackifiers or also fertilizers or other active substances for achieving specific effects.

The examples below are intended to illustrate the invention in greater detail without imposing any restriction.

1. PREPARATION EXAMPLES

1.1 Preparation of N-(4-methyl-6-cyclopropylpyrimidin-2-yl)-phenylhydroxylamine

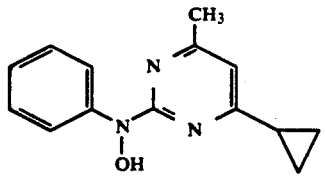

4.22 g (0.025 mol) of 2-chloro-4-methyl-6-cyclopropylpyrimidine and 3.06 g (0.028 mol) of phenylhydroxylamine are dissolved in 25 ml of methanol, 2 ml of acetic acid are added, and the solution is allowed to stand overnight at room temperature. After this, starting pyrimidine is no longer detectable in the thin-layer chromatogram. The mixture is poured into water mixed with ethyl acetate, stirred, and rendered neutral to a pH of 7 using sodium hydrogen carbonate. The organic phase is separated off and re-extracted twice, the extracts are dried using sodium sulfate, and the solvent is removed on a rotary evaporator, which gives 6.5 g of crude product whose recrystallization from 16 ml of ethyl acetate yields 3.77 g (62.5% of theory) of pure product; m.p. 121.5°–123° C. A further 0.73 g of pure substance are obtained from the mother liquor, so that the total yield is increased to 74.6% of theory.

| Analysis of $C_{14}H_{15}N_3O$ (M = 241.29) | | |
|---|---|---|
| | % calc. | % found |
| C | 69.69 | 69.83 |
| H | 6.27 | 6.16 |
| N | 17.42 | 16.93 |
| O | 6.63 | 7.13 |

1.2 Preparation of N-(4-methyl-6-methoxymethylpyrimidin-2-yl)-3-fluorophenyl hydroxylamine

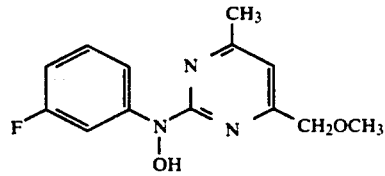

4.32 g (0.025 mol) of 2-chloro-4-methyl-6-methoxymethylpyrimidine in 25 ml of methanol and 2 ml of glacial acetic acid are treated at room temperature with 3.81 g (0.03 mol) of 3-fluorophenylhydroxylamine. The reaction starts up only slowly and proceeds at a higher rate after 2 ml of concentrated aqueous hydrochloric acid have been added (thin-layer chromatography). When all of the starting pyrimidine has reacted, the mixture is worked up by extraction with water and ethyl acetate to give the crude product (6.7 g). Chromatographic working-up of the latter (silica gel; mobile phase 25 parts of ethyl acetate and 75 parts of hexane) gives 4.59 g (69.7% of theory) of pure substance as an oil. For NMR data, see Table 2.

| Analysis $C_{13}H_{14}FN_3O_2$ (M = 263.27) | | |
|---|---|---|
| | % calc. | % found |
| C | 59.31 | 59.44 |
| H | 5.36 | 5.52 |
| N | 15.96 | 15.60 |
| O | 7.22 | 7.28 |

1.3 Preparation of O-propargyl-N-(4-methyl-6-cyclopropylpyrimidin-2-yl)-phenylhydroxylamine

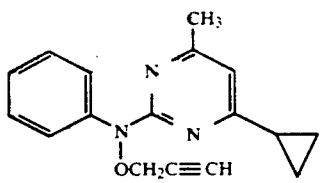

1.32 g (0.0055 mol) of N-(4-methyl-6-cyclopropyl-pyrimidin-2-yl)-phenylhydroxylamine are stirred with 0.72 g (0.006 mol) of propargyl bromide and 0.2 g of cetyltrimethylammonium bromide in 10 ml of methylene chloride and 5 ml of 30% sodium hydroxide solution for 60 minutes at room temperature. The alkylation process proceeds to completion (thin-layer chromatography). Extraction with water and chloroform leads to a crude product whose purification by means of column chromatography (silica gel; mobile phase a mixture of 20 parts of ethyl acetate and 80 parts of hexane) gives 1.55 g of pure substance as an oil. For NMR data, see Table 2.

| Analysis $C_{17}H_{17}N_3O$ (M = 279.34) | | |
|---|---|---|
| | % calc. | % found |
| C | 73.10 | 72.91 |
| H | 6.14 | 6.11 |
| N | 15.04 | 14.94 |

1.4 Preparation of O-methylcarbamyl-N-(4-methyl-6-cyclopropylpyrimidin-2-yl)-phenylhydroxylamine

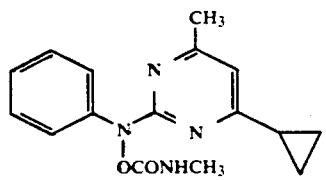

3.14 g (0.013 mol) of N-(4-methyl-6-cyclopropylpyrimidin-2-yl)-phenylhydroxylamine and 0.86 g (0.015 mol) of methyl isocyanate are dissolved in 40 ml of tetrahydrofuran and the solution is treated with a few drops of triethylamine. The reaction is carried out at room temperature in the course of 1 hour. The solvent is removed on a rotary evaporator and the residue is recrystallised from a mixture of 4 ml of toluene and 6 ml of cyclohexane. Yield: 3.60 g (92.7% of theory); m.p. 96°-97° C.

| Analysis $C_{16}H_{18}N_4O_2$ (M = 298.35) | | |
|---|---|---|
| | % calc. | % found |
| C | 64.41 | 64.40 |
| H | 6.08 | 6.15 |
| N | 18.78 | 18.91 |

1.5 Preparation of O-propionyl-N-(4-methyl-6-methoxymethylpyrimidin-2-yl)-3-fluorophenylhydroxylamine

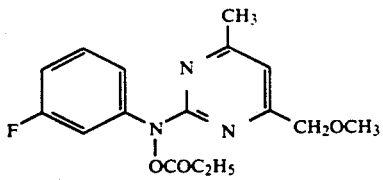

2.49 g (0.0095 mol) of N-(4-methyl-6-methoxymethyl-pyrimidin-2yl)-3-fluorophenylhydroxylamine and 1.5 g of triethylamine are dissolved in 30 ml of tetrahydrofuran, and the solution is treated dropwise with a solution of 1.16 g (0.0125 mol) of propionyl chloride in 10 ml of tetrahydrofuran at not more than 10° C. Triethylamine hydrochloride separates out. The mixture is extracted with water and chloroform and, after the solvents have been removed, 3.71 g of crude product are obtained which are purified by means of column chromatography. The pure yield is 1.99 g of oil (65.7% of theory). For NMR data, see Table 2.

| Analysis $C_{16}H_{18}FN_3O_3$ (M = 319.34) | | |
|---|---|---|
| | % calc. | % found |
| C | 60.18 | 59.84 |
| H | 5.68 | 5.60 |
| N | 13.16 | 13.45 |
| F | 5.95 | 6.01 |

1.6 Preparation of O-diethylcarbamyl-N-(4-methyl-6-cyclopropylpyrimidin-2-yl)-3-fluorophenylhydroxylamine

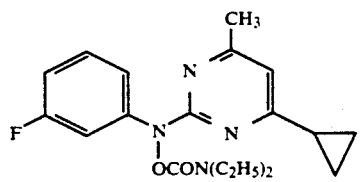

2.20 g (0.0085 mol) of N-(4-methyl-6-cyclopropyl-pyrimidin-2-yl)-3-fluorophenylhydroxylamine and 1.33 g (0.0098 mol) of diethylcarbamoyl chloride are dissolved in 20 ml of tetrahydrofuran and 1.12 g (0.011 mol) of triethylamine are added. Only after the addition of 0.20 g of dimethylaminopyridine does the reaction start, on boiling, and proceeds smoothly to completion. The mixture is extracted with water and ethyl acetate, and the crude product is isolated and purified by column chromatography. Yield 3.07 g of an oil. For NMR data, see Table 2.

| Analysis $C_{19}H_{23}FN_4O_2$ | | |
|---|---|---|
| | % calc. | % found |
| C | 63.67 | 63.79 |
| H | 6.47 | 6.67 |
| N | 15.63 | 15.36 |
| F | 5.30 | 5.29 |

1.7 Preparation of O-carbomethoxy-N-(4-methyl-6-cyclopropylpyrimidin-2-yl)-3-fluorophenylhydroxylamine

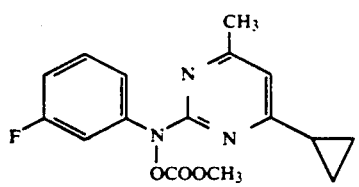

3.89 g (0.015 mol) of N-(4-methyl-6-cyclopropylpyrimidin-2-yl)-3-fluorophenylhydroxylamine and 2.20 g (0.02 mol) of triethylamine are dissolved in 20 ml of tetrahydrofuran, and a solution of 1.56 g (0.0165 mol) of methyl chloroformate in 8 ml of tetrahydrofuran are added dropwise at room temperature with cooling. Triethylamine hydrochloride immediately precipitates. The mixture is extracted with ethyl acetate, and the crude product is purified by column chromatography on silica gel. 4.40 g of product are obtained, and this is recrystallised from 15 ml of n-hexane and 6 ml of ethyl acetate. The yield is 4.10 g (86% of theory); m.p. 59°–60° C.

| Analysis $C_{16}H_{16}FN_3O_3$ (MW 317.32) | | |
|---|---|---|
| | % calc. | % found |
| C | 60.56 | 60.74 |
| H | 5.08 | 5.18 |
| N | 13.24 | 13.43 |
| F | 5.99 | 6.08 |

TABLE 1

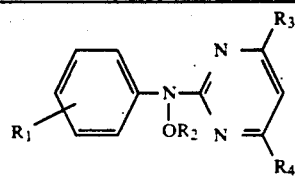

| Comp. No | $R_1$ | $R_2$ | $R_3$ | $R_4$ | Physical constants |
|---|---|---|---|---|---|
| 1.1 | H | H | $CH_3$ | $CH_3$ | M.p. 122–123° C. |
| 1.2 | H | H | $CH_3$ | $C_2H_5$ | |
| 1.3 | H | H | $CH_3$ | n-$C_3H_7$ | |
| 1.4 | H | H | $C_2H_5$ | $CH(CH_3)_3$ | |
| 1.5 | 4-Cl | H | n-$C_3H_7$ | $C(CH_3)_3$ | |
| 1.6 | 3-F | H | $CH_3$ | $CH_3$ | M.p. 142–143° C. |
| 1.7 | 3-F | $COCH_3$ | $CH_3$ | $CH_3$ | See Table 2 |
| 1.8 | H | $OC_2H_5$ | $CH_3$ | $CH_3$ | |
| 1.9 | 4-$CH_3O$ | n-$C_3H_7$NHCO | $CH_3$ | $CH_3$ | |
| 1.10 | 3-$CF_3$ | $C_6H_5$NHCO | $CH_3$ | $CH_3$ | |
| 1.11 | 3-$CF_3$ | 4-$CF_3$—$C_6H_4$NHCO | $C_2H_5$ | $C_2H_5$ | |
| 1.12 | H | $COOCH_3$ | $CH_3$ | $CH_3$ | |
| 1.13 | H | H | $CH_3$ | cyclo-$C_3H_5$ | M.p. 121–123° C. |
| 1.14 | H | H | $CH_3$ | ◁CH_3 | |
| 1.15 | H | $COSCH_3$ | $CH_3$ | $CH_3$ | |
| 1.16 | 3-F | H | cyclo-$C_3H_5$ | $CH_3$ | M.p. 124–126° C. |
| 1.17 | H | $CH_3$ | cyclo-$C_3H_5$ | $CH_3$ | See Table 2 |
| 1.18 | 4-$CH_3$ | H | $CH(CH_3)_2$ | $CH_3$ | |
| 1.19 | 4-$CH_3$ | $SO_2C_2H_5$ | $CH_3$ | $CH_3$ | |
| 1.20 | 4-$CH_3$ | $COCF_3$ | $CH_3$ | $CH_3$ | |
| 1.21 | 4-$CH_3$ | $CSSCH_3$ | $CH_3$ | $CH_3$ | |
| 1.22 | H | $CH_2C_6H_5$ | $CH_3$ | cyclo-$C_3H_5$ | See Table 2 |
| 1.23 | H | $Si(CH_3)_3$ | $CH_3$ | cyclo-$C_3H_5$ | |
| 1.24 | H | $COCF_3$ | $C_2H_5$ | cyclo-$C_3H_5$ | |
| 1.25 | H | $PO(OC_2H_5)_2$ | $CH_3$ | cyclo-$C_3H_5$ | |
| 1.26 | H | $COCH_3$ | $CH_3$ | cyclo-$C_3H_5$ | See Table 2 |
| 1.27 | 3-F | H | $CH_2OCH_3$ | $CH_3$ | See Table 2 |
| 1.28 | 4-F | $C_4H_9$-n | $CH_2OC_2H_5$ | $C_2H_5$ | |
| 1.29 | H | H | —C≡$CCH_3$ | $CH_3$ | |
| 1.30 | 3-F | H | —C≡$CCH_3$ | $CH_3$ | |
| 1.31 | 4-F | H | —C≡$CCH_3$ | n-$C_3H_7$ | |
| 1.32 | 3-F | $COC_2H_5$ | $CH_3$ | $CH_2OCH_3$ | See Table 2 |
| 1.33 | 3-F | $COOCH_3$ | cyclo-$C_3H_5$ | $CH_3$ | M.p. 59–60° C. |
| 1.34 | H | $COSCH_3$ | cyclo-$C_3H_5$ | $CH_3$ | |
| 1.35 | H | $CSSCH_3$ | cyclo-$C_3H_5$ | $CH_3$ | |
| 1.36 | H | $COC(CH_3)_3$ | cyclo-$C_3H_5$ | $CH_3$ | See Table 2 |
| 1.37 | H | $CONHCH_3$ | cyclo-$C_3H_5$ | $CH_3$ | M.p. 96–97° C. |
| 1.38 | H | $SiC(CH_3)_2C(CH_3)_3$ | cyclo-$C_3H_5$ | $CH_3$ | |
| 1.39 | 3-F | $Si(CH_3)_3$ | cyclo-$C_3H_5$ | $CH_3$ | B.p. 145° C./6.5 Pa |
| 1.40 | 3-F | $CH_2CH_2CN$ | cyclo-$C_3H_5$ | $CH_3$ | M.p. 54–55° C. |
| 1.41 | H | $CH_2CH_2OCH_3$ | n-$C_4H_9$ | $CH_3$ | |
| 1.42 | 2-Cl | $CH_2C$≡$CCH_3$ | $CH_3$ | $C_2H_5$ | |
| 1.43 | H | $CH_2C$≡$CH$ | $CH_3$ | cyclo-$C_3H_5$ | See Table 2 |
| 1.44 | 3-F | $SO_2CH_3$ | $CH_3$ | cyclo-$C_3H_5$ | |
| 1.45 | H | 4-$CH_3$—$C_6H_4SO_2$ | $CH_3$ | cyclo-$C_3H_5$ | |
| 1.46 | 3-F | $CH_3$ | $CH_3$ | cyclo-$C_3H_5$ | See Table 2 |
| 1.47 | H | $CON(C_2H_5)_2$ | $CH_3$ | cyclo-$C_3H_5$ | |

TABLE 1-continued

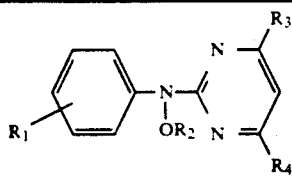

| Comp. No | R₁ | R₂ | R₃ | R₄ | Physical constants |
|---|---|---|---|---|---|
| 1.48 | 3-F | CON(CH₃)₂ | CH₃ | cyclo-C₃H₅ | |
| 1.49 | H | 4-Cl—C₆H₄CO | CH₃ | cyclo-C₃H₅ | |
| 1.50 | 3-F | n-C₃H₇ | CH₃ | cyclo-C₃H₅ | See Table 2 |
| 1.51 | 3-CH₃O | COC≡CH | CH₃ | CH₃ | |
| 1.52 | 2-I | COCH=CHCH₃ | CH₃ | CH₃ | |
| 1.53 | H | H | —CH=CHCH₃ | CH₃ | |
| 1.54 | 3-F | CON(C₂H₅)₂ | cyclo-C₃H₅ | CH₃ | See Table 2 |
| 1.55 | 4-F | H | cyclo-C₃H₅ | CH₃ | |
| 1.56 | 4-F | COCH₃ | cyclo-C₃H₅ | CH₃ | |
| 1.57 | 4-F | CON(CH₃)₂ | cyclo-C₃H₅ | CH₃ | |
| 1.58 | 3-F | CONHC₃H₇(n) | cyclo-C₃H₅ | CH₃ | M.p. 118-119° C. |
| 1.59 | 3-F | COOC₆H₅ | cyclo-C₃H₅ | CH₃ | M.p. 71-72° C. |
| 1.60 | H | COOCH₂CCl₃ | cyclo-C₃H₅ | CH₃ | |
| 1.61 | H | H | CH₂OCH₃ | CH₃ | |
| 1.62 | H | COCH₃ | CH₂OCH₃ | CH₃ | |
| 1.63 | H | H | C₂H₅ | C₂H₅ | |
| 1.64 | H | H | n-C₃H₇ | C₂H₅ | |
| 1.65 | H | CON(CH₃)₂ | CH₂OCH₃ | CH₃ | |
| 1.66 | H | CSNHCH₃ | CH₂OCH₃ | CH₃ | |
| 1.67 | 3-F | H | CF₃ | CH₃ | M.p. 104-105° C. |
| 1.68 | H | CONHCH₃ | CH₃ | CH₂OCH₃ | |
| 1.69 | H | H | n-C₃H₇ | n-C₃H₇ | |
| 1.70 | 3-F | 3-Cl—C₆H₄NHCO | cyclo-C₃H₅ | CH₃ | M.p. 122-123° C. |
| 1.71 | 3-F | H | CH₃ | ⊲CH₃ | M.p. 108-110° C. |
| 1.72 | H | H | CH(CH₃)₂ | CH(CH₃)₂ | |
| 1.73 | H | COOCH₃ | CH₂OCH₃ | CH₃ | |
| 1.74 | 3-F | H | C₂H₅ | cyclo-C₃H₅ | M.p. 88-89° C. |
| 1.75 | 3-F | COC(CH₃)₃ | CH₃ | cyclo-C₃H₅ | See Table 2 |
| 1.76 | 3-F | CO—C₆H₄—CH₃ | CH₃ | cyclo-C₃H₅ | M.p. 83-84° C. |
| 1.77 | 3-F | H | CH₂OCH₃ | cyclo-C₃H₅ | M.p. 107-109° C. |

TABLE 2

NMR data of non-crystallising compounds

| Comp. No. | NMR; values in ppm; |
|---|---|
| 1.7 | 2.29s(COCH₃); 2.35s(2CH₃, pyrim.), 6.55s(H₅-pyrim.); 6.6-7.6m(arom.H) |
| 1.17 | 0.8-1.1m(—CH₂CH₂—); 1.5-1.9m(CH); 2.38s(C—CH₃); 3.90s(OCH₃); 6.53s(H₅-pyrim.); 7.1-7.8m(arom.H) |
| 1.22 | 1.1-1.5t(CH₃CH₂); 2.40s(CH₃, pyrim.); 2.6q(CH₂CH₃); 3.43s(OCH₃); 4.38s(CH₂O); 6.87s(H₅-pyrim.) |
| 1.26 | 0.8-1.1m(CH₂CH₂); 1.7-2.0m(CH); 2.25s(CH₃CO); 2.32s(CH₃-pyrim.); 6.60s(H₅-pyrim.) |
| 1.27 | 2.33s(CH₃-pyrim.); 3.37s(OCH₃); 4.30s(OCH₂); 6.73s(H₅-pyrim.) |
| 1.32 | 1.30t(CH₂CH₃); 2.63q(CH₂CH₃); 2.40s(CH₃-pyrim.); 3.45s(OCH₃); 4.38s(OCH₂); 6.87s(H₅-pyrim.) |
| 1.36 | 0.9-1.2m(CH₂CH₂); 1.37s(C(CH₃)₃); 1.5-1.9m(CH); 2.27s(CH₃); 6.52s(H₅-pyrim.) |
| 1.43 | 0.8-1.1m(CH₂CH₂); 1.6-2.0m(CH); 2.37(CH₃); 2.45t(HC≡C—); 4.80d(CH₂C≡C); 6.60s(H₅-pyrim.) |
| 1.46 | 0.8-1.1m(CH₂CH₂); 1.5-2.0m(CH); 2.40s(CH₃-pyrim.); 3.92s(OCH₃); 6.60s(H₅-pyrim.) |
| 1.50 | 1.03 t+m(CH₃, CH₂CH₂); 1.5-2.0m(CH₂, CH); 2.40s(CH₃-pyrim.), 4.03t(OCH₂); 6.60s(H₅-pyrim.) |
| 1.54 | 0.7-1.3 t+m(CH₃, CH₂CH₂); 1.5-2.0m(CH); 2.33s(CH₃); 3.47q(CH₂CH₃); 6.60s(H₅-pyrim.) |
| 1.75 | 0.7-1.2m(CH₂CH₂); 1.4s(C(CH₃)₃); 2.32s(CH₃); 6.68s(H₅-pryim.); 7.2-7.6m(arom.H) |

2. Formulation examples of liquid active substances of the formula I (% = % by weight)

2.1. Emulsion concentrates

| | a | b | c |
|---|---|---|---|
| Active substance from Table 1 | 25% | 40% | 50% |
| Calcium dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |
| Cyclohexanone | — | 15% | 20% |
| Xylene mixture | 65% | 25% | 20% |

Emulsions of any desired concentration can be prepared from concentrates by diluting them with water.

2.2. Solutions

| | a | b | c | d |
|---|---|---|---|---|
| Active substance from Table 1 | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Petroleum ether (boiling range 160-190°C.) | — | — | 94% | — |

(MW = molecular weight)

The solutions are suitable for use in the form of very small droplets.

| 2.3. Granules | a | b |
|---|---|---|
| Active substance from Table 1 | 5% | 10% |
| Kaolin | 94% | — |
| Highly disperse silica | 1% | — |
| Attapulgite | — | 90% |

The active substance is dissolved in methylene chloride, the solution is sprayed on to the carrier, and the solvent is subsequently evaporated in vacuo.

| 2.4. Dusts | a | b |
|---|---|---|
| Active substance from Table 1 | 2% | 5% |
| Highly disperse silica | 1% | 5% |
| Talc | 97% | — |
| Kaolin | — | 90% |

Ready-to-use dusts are obtained by intimately mixing the carriers with the active substance.

Formulation examples of solid substances of the formula I (% = % by weight)

| 2.5. Wettable powders | a | b | c |
|---|---|---|---|
| Active substance from Table 1 | 25% | 50% | 75% |
| Sodium ligninsulfonate | 5% | 5% | — |
| Sodium laurylsulfate | 3% | — | 5% |
| Sodium diisobutylnaphthalene-sulfonate | — | 6% | 10% |
| Octylphenol polyethylene glycol ether (7-8 mol of ethylene oxide) | — | 2% | — |
| Highly disperse silica | 5% | 10% | 10% |
| Kaolin | 62% | 27% | — |

The active substance is thoroughly mixed with the additives and thoroughly ground in a suitable mill. This gives wettable powders which can be diluted with water to give suspensions of any desired concentration.

| 2.6. Emulsion concentrate | |
|---|---|
| Active substance from Table 1 | 10% |
| Octylphenol polyethylene glycol ether (4-5 mol of ethylene oxide) | 3% |
| Calcium dodecylbenzene sulfonate | 3% |
| Castor oil polyglycol ether (35 mol of ethylene oxide) | 4% |
| Cyclohexanone | 34% |
| Xylene mixture | 50% |

Emulsions of any desired concentration can be prepared from this concentrate by diluting it with water.

| 2.7. Dusts | a | b |
|---|---|---|
| Active substance from Table 1 | 5% | 8% |
| Talc | 95% | — |
| Kaolin | — | 92% |

Ready-to-use dusts are obtained by mixing the active substance with the carrier and grinding the mixture on a suitable mill.

| 2.8. Extruder granules | |
|---|---|
| Active substance from Table 1 | 10% |
| Sodium ligninsulfonate | 2% |
| Carboxymethylcellulose | 1% |

-continued

| 2.8. Extruder granules | |
|---|---|
| Kaolin | 87% |

The active substance is mixed with the additives, and the mixture is ground and moistened with water. This mixture is extruded and subsequently dried in a stream of air.

| 2.9. Coated granules | |
|---|---|
| Active substance from Table 1 | 3% |
| Polyethylene glycol (MW 200) | 3% |
| Kaolin | 94% |

(MW = molecular weight)

The kaolin is moistened with polyethylene glycol and the finely ground active substance is applied uniformly thereto in a mixer. Dust-free coated granules are obtained in this manner.

| 2.10. Suspension concentrate | |
|---|---|
| Active substance from Table 1 | 40% |
| Ethylene glycol | 10% |
| Nonylphenol polyethylene glycol ether (15 mol of ethylene oxide) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active substance is mixed intimately with the additives. This gives a suspension concentrate from which suspensions of any desired concentration can be prepared by diluting it with water.

3. BIOLOGICAL EXAMPLES

Example 3.1: Action Against *Venturia Inaequalis* on Apple Shoots

Residual-Protective Action

Apple cuttings which have recent shoots 10-20 cm in length are sprayed with a spray liquor prepared with a wettable powder of the active substance (0.006% of active ingredients). After 24 hours, the treated plants are infected with a conidia suspension of the fungus. The plants are then incubated for 5 days at 90-100% relative atmospheric humidity and placed in a greenhouse at 20°-24° C. for 10 further days. The plants are scored for scab 15 days after infection.

Compounds from Table 1 have a good activity against Venturia (infestation: less than 20%). For example, the compounds Nos. 1.13, 1.16, 1.17, 1.26, 1.36 and 1.37 reduce Venturia infestation to 0 to 10%. In contrast, infestation with Venturia of untreated but infected control plants is 100%.

Example 3.2: Action Against *Botrytis Cinerea* on Apple Fruits

Residual-Protective Action

Artificially damaged apples are treated by applying a spray liquor prepared with a wettable powder of the active substance (0.002% of active ingredient) dropwise to the damaged sites. The treated fruits are subsequently inoculated with a spore suspension of the fungus and incubated for one week at higher atmospheric humidity and about 20° C. For scoring, the damaged sites which show signs of rot are counted, and the fungicidal action of the test substance is calculated therefrom.

Compounds from Table 1 have a good activity against Botrytis (attack: less than 20%). For example, the compounds Nos. 1.1, 1.6, 1.7, 1.13, 1.16, 1.17, 1.22, 1.27, 1.32, 1.36, 1.37 and 1.54 reduce Botrytis attack to 0 to 10%. In contrast, attack by Botrytis of untreated but infected control plants is 100%.

Example 3.3: Action Against Erysiphe Graminis on Barley a) Residual-Protective Action Barley plants about 8 cm in height are sprayed with a spray liquor prepared with a wettable powder of the active substance (0.006% of active ingredient). After 3-4 hours, the treated plants are dusted with conidia of the fungus. The infected barley plants are placed in a greenhouse at about 22° C. and scored for fungal attack after 10 days.

Compounds from Table 1 have a good activity against Erysiphe (attack: less than 20%). For example, the compounds Nos. 1.1, 1.16, 1.26 and 1.36, reduce Erysiphe attack to 0 to 10%. In contrast, attack by Erysiphe of untreated but infected control plants is 100%.

What is claimed is:

1. A compound of the formula I

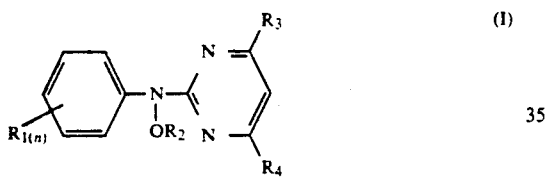

in which $R_1$ is hydrogen, halogen, methyl, methoxy or trifluoromethyl; n is 1 or 2; $R_2$ is hydrogen, $C_1-C_6$alkyl, $C_1-C_3$alkyl which is substituted by halogen, cyano or methoxy, or is $C_2-C_5$alkenyl, $C_2-C_5$alkynyl, benzyl, $COR_5$, $CON(R_5)R_6$, $CSN(R_5)R_6$, $CO(OR_6)$, $CO(SR_6)$, $CS(SR_5)$, $SO_2R_7$, $PO(OR_6)_2$ or $Si(R_6)_3$; $R_3$ and $R_4$ independently of one another are hydrogen, $C_1-C_5$alkyl, $CH_2OR_6$, cyclopropyl, methylcyclopropyl, $C_2-C_5$alkenyl, $C_2-C_5$alkynyl or $C_1-C_2$haloalkyl; $R_5$ is hydrogen, $C_1-C_6$alkyl, $C_1-C_3$alkyl which is substituted by 1 to 3 halogens, $C_1-C_3$alkyl which is substituted by $OR_6$ or $SR_6$, or is $C_2-C_5$alkenyl, $C_2-C_5$alkenyl which is substituted by 1 to 3 halogens, $C_2-C_5$alkynyl, $C_3-C_6$cycloalkyl, phenyl or phenyl which is monosubstituted to trisubstituted by halogen, $C_1-C_3$alkyl, $C_1-C_3$haloalkyl, $C_1-C_3$alkoxy, nitro or cyano; $R_6$ is $C_1-C_6$alkyl; $R_7$ is $C_1-C_3$alkyl, phenyl, phenyl which is monosubstituted or disubstituted by halogen, $C_1-C_2$alkyl, $C_1-C_2$haloalkyl, methoxy or nitro; including the acid addition salts of the compounds of the formula I.

2. A compound according to claim 1, of the formula I, in which $R_1$ is hydrogen, fluorine, chlorine or bromine; n is 1; $R_2$ is hydrogen, $C_1-C_4$alkyl, $C_1-C_3$alkenyl, $C_1-C_3$alkynyl, $COR_5$, $CON(R_5)R_6$, $CSNR_5(R_6)$ or $COOR_6$; $R_3$ and $R_4$ independently of one another are hydrogen, $C_1-C_5$alkyl, methoxymethyl, cyclopropyl or methylcyclopropyl; $R_5$ is hydrogen, $C_1-C_6$alkyl, $C_3-C_6$cycloalkyl, $C_2-C_5$alkenyl, $C_2-C_5$alkynyl, phenyl, or phenyl which is monosubstituted by fluorine, chlorine, bromine, methyl, trifluoromethyl, trichloromethyl, tribromomethyl, methoxy, nitro or cyano; and $R_6$ is $C_1-C_3$alkyl.

3. A compound according to claim 1, of the formula I, in which $R_1$ is hydrogen, fluorine or chlorine; n is 1; $R_2$ is hydrogen, $C_1-C_3$alkyl, $COR_5$, $CON(R_5)R_6$, $CSNR_5(R_6)$ or $COOR_6$; $R_3$ and $R_4$ independently of one another are $C_1-C_3$alkyl, methoxymethyl, cyclopropyl or methylcyclopropyl; $R_5$ is hydrogen or $C_1-C_4$alkyl; and $R_6$ is $C_1-C_3$alkyl.

4. A compound of the formula I, according to claim 1, selected from the group comprising:
N-(4,6-dimethylpyrimidin-2-yl)-phenylhydroxylamine
N-(4,6-dimethylpyrimidin-2-yl)-3-fluorophenylhydroxylamine
N-(4-methyl-6-cyclopropylpyrimidin-2-yl)-phenylhydroxylamine
N-(4-methyl-6-cyclopropylpyrimidin-2-yl)-3-fluorophenylhydroxylamine
N-(4-methyl-6-methoxymethylpyrimidin-2-yl)-phenylhydroxylamine
N-(4-methyl-6-methoxymethylpyrimidin-2-yl)-3-fluorophenylhydroxylamine
O-acetyl-N-(4-methyl-6-cyclopropylpyrimidin-2-yl)-phenylhydroxylamine
O-pivaloyl-N-(4-methyl-6-cyclopropylpyrimidin-2-yl)-phenylhydroxylamine.

5. A process for the preparation of compounds of the formula I, which comprises reacting:

A) a pyrimidinyl halide of the formula II

with a phenylhydroxylamine of the formula III

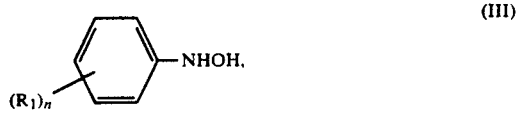

in which $R_1$, $R_3$ and $R_4$ and n are as defined under formula I and Hal is a halogen, preferably chlorine or bromine, in the presence of an acid in inert organic solvents, at temperatures from $-30°$ to $100°$ C., preferably 0° to 50° C.; and B) the resulting compound Ia

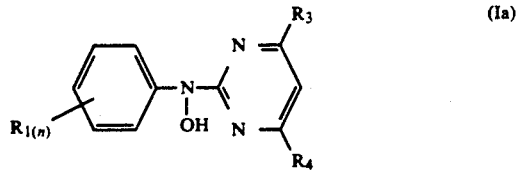

D) with an anhydride of the formula V

in inert organic solvents, at temperatures from $-20°$ to $150°$ C., and in the presence of an acid-binding agent.

6. A composition for controlling or preventing infestation by harmful microorganisms, which comprises, as the active component, an effective amount of at least one compound of the formula I according to claim 1, plus a suitable carrier or other adjuvant.

7. A composition for controlling or preventing infestation by harmful microorganisms, which comprises, as the active component, an effective amount of at least one compound of the formula I according to claim 2, plus a suitable carrier or other adjuvant.

8. A composition for controlling or preventing infestation by harmful microorganisms, which comprises, as the active component, an effective amount of at least one compound of the formula I according to claim 3, plus a suitable carrier or other adjuvant.

9. A composition for controlling or preventing infestation by harmful microorganisms, which comprises, as the active component, an effective amount of at least one compound of the formula I according to claim 4, plus a suitable carrier or other adjuvant.

10. A method of controlling or preventing infestation of crop plants by phytopathogenic microorganisms, which comprises applying, as the active substance, a compound of the formula I according to claim 1 to the plant, parts of the plant or the site where it grows.

11. A method according to claim 10, in which phytopathogenic fungi are controlled.

12. A method of controlling or preventing infestation of crop plants by phytopathogenic microorganisms, which comprises applying, as the active substance, a compound of the formula I according to claim 2 to the plant, parts of the plant or the site where it grows.

13. A method of controlling or preventing infestation of crop plants by phytopathogenic microorganisms, which comprises applying, as the active substance, a compound of the formula I according to claim 3 to the plant, parts of the plant or the site where it grows.

14. A method of controlling or preventing infestation of crop plants by phytopathogenic microorganisms, which comprises applying, as the active substance, a compound of the formula I according to claim 4 to the plant, parts of the plant or the site where it grows.

* * * * *